(12) United States Patent
O'Brien (10) Patent No.: US 8,568,327 B2
(45) Date of Patent: Oct. 29, 2013

(54) MONITORING DEVICE AND METHOD

(75) Inventor: Terence Kevin O'Brien, Cambridgeshire (GB)

(73) Assignee: LiDCO Group, PLC, London (GB)

( * ) Notice: Subject to any disclaimer, the term of this patent is extended or adjusted under 35 U.S.C. 154(b) by 590 days.

(21) Appl. No.: 12/770,856

(22) Filed: Apr. 30, 2010

(65) Prior Publication Data
US 2011/0270047 A1 Nov. 3, 2011

(51) Int. Cl.
*A61B 5/02* (2006.01)
(52) U.S. Cl.
USPC ............................................ 600/483; 600/544
(58) Field of Classification Search
USPC .................... 600/301, 544, 545, 483
See application file for complete search history.

(56) References Cited

U.S. PATENT DOCUMENTS

| | | | |
|---|---|---|---|
| 6,071,244 A | 6/2000 | Band et al. | |
| 2003/0055356 A1 | 3/2003 | Nonaka | |
| 2003/0144600 A1 | 7/2003 | Yarita | |
| 2006/0206011 A1* | 9/2006 | Higgins et al. | 600/300 |
| 2006/0224067 A1 | 10/2006 | Giftakis et al. | |
| 2008/0045809 A1 | 2/2008 | Hermannsson | |
| 2008/0319275 A1* | 12/2008 | Chiu et al. | 600/300 |
| 2009/0005655 A1 | 1/2009 | Frank et al. | |
| 2009/0005703 A1* | 1/2009 | Fasciano | 600/561 |
| 2009/0018462 A1* | 1/2009 | Bell | 600/544 |
| 2009/0076339 A1 | 3/2009 | Quintin et al. | |
| 2009/0099424 A1* | 4/2009 | O'Brien et al. | 600/301 |
| 2009/0124867 A1* | 5/2009 | Hirsh et al. | 600/301 |
| 2009/0131805 A1 | 5/2009 | O'Brien et al. | |
| 2009/0177108 A1 | 7/2009 | Shieh | |
| 2010/0256515 A1* | 10/2010 | Egeth | 600/544 |
| 2011/0087117 A1 | 4/2011 | Tremper et al. | |

FOREIGN PATENT DOCUMENTS

| | | |
|---|---|---|
| WO | 02100267 | 12/2002 |
| WO | 2011044408 | 4/2011 |

OTHER PUBLICATIONS

International Search Report for PCT/GB2011/000651 dated Jul. 22, 2011.
Search Report for GB1007331.0 dated Aug. 19, 2010.
Search Report for GB1007331.0 dated Dec. 21, 2010.

* cited by examiner

*Primary Examiner* — Patricia Mallari
*Assistant Examiner* — Etsub Berhanu
(74) *Attorney, Agent, or Firm* — Nixon Peabody LLP (57) ABSTRACT

A monitoring device arranged to display a level of consciousness and hemodynamic parameters of a patient for simultaneous viewing. A dependence of changes in the hemodynamic parameters of the patient on the level of consciousness of the patient may be more easily observed using the monitoring device. Correlations between the patient's level of consciousness and the patient's hemodynamic parameters may further be determined and displayed to aid clinicians in estimating any improvement in hemodynamic parameters that may be achieved through manipulation of the patient's level of consciousness, fluid status and drugs.

11 Claims, 7 Drawing Sheets

MONITORING DEVICE AND METHOD

FIELD OF THE INVENTION

The present invention relates to an apparatus and method for hemodynamic monitoring. The present invention in particular relates to an apparatus and method suitable for hemodynamic monitoring during surgery, sedation/anaesthesia and/or induction of sedation/anaesthesia.

BACKGROUND

It is known that the blood pressure of surgery patients falls from a pre-anaesthetic induction level to a lower level during induction of sedation/anaesthesia. This reduction in blood pressure has to be corrected by the anaesthetist to at least a level that is likely to reliably support the patient's vital functions.

The drop in blood pressure through the anaesthetic induction phase is widely viewed as being the result of a fall in systemic vascular resistance (SVR; SVR=[((mean arterial pressure−central venous pressure)*80)/cardiac output)]; the unit normally used for expressing SVR is dynes*s*cm-5) due to the administered anaesthetic drug(s) causing a vasodilatory response of the arterial tree. The arteries and pre-capillary arterioles provide about two thirds of the resistance to flow in the vascular system. Arterial vasodilation increases arterial capacity and consequently reduces the affected vasculature's resistance to blood flow. As the mean arterial pressure (MAP) is the product of cardiac output (CO) and systemic vascular resistance (MAP=CO*SVR), a reduction in SVR brings about a corresponding blood pressure reduction if the cardiac output remains the same.

While a fall in blood pressure can be caused by arterial vasodilation and the above discussed associated decrease in systemic vascular resistance, a number of other factors also influence blood pressure. Changes in cardiac output can also affect blood pressure/MAP. Cardiac output (expressed in l/min) is the product of stroke volume (SV, expressed in ml) and heart rate (HR, expressed in bpm). A fall in heart rate will therefore reduce cardiac output and arterial blood pressure.

Cardiac stroke volume in turn is affected by a number of factors. One of these factors is the extent to which the left ventricle is filled before contraction. This factor is often referred to as preload. In the healthy heart the fuller the ventricle is before systole (contraction) the more that the ejected stroke volume will increase—up to a limit, as can be seen from the Frank Starling curve. The dependence of the filling of the left ventricle on the efficient venous return of blood to the right side of the heart is often referred to as preload dependence. If the venous blood flow to the heart is insufficient to adequately fill the left ventricle prior to its contraction, then the stroke volume is reduced.

The major collecting veins contain 64% of the total circulating blood volume. The diameter and tone of the major collection veins is adjusted through hormonal/neural effects on the vein's smooth muscle component. Drugs may influence the major collection veins' tone and capacitance. Dilation of the major collection veins and/or blood loss will reduce preload and consequently also stroke volume.

Another factor affecting blood pressure is the resistance to the ejection of blood from the left ventricle across the aortic valve into the systemic arterial circulation. This resistance can be considered the sum of all forces opposing ventricular muscle shortening. This factor is often referred to as afterload and is regularly (and incorrectly) considered to be the same/similar to systemic vascular resistance (SVR). A simple example can show that afterload and SVR are in fact not the same. If two patients with equal ventricular dimensions are considered, wherein the first patient has a MAP of 60 mmHg and a cardiac output of 4 l/min and the second patient has a MAP of 120 mmHg and a cardiac output of 8 l/min. Both of these patients will have the same SVR. The resistance to the ejection of blood from the left ventricle, however, differs by a factor of two, as is evident from the difference in MAP.

If the left ventricle is working in a preload dependent fashion then the ventricular internal fibre load applied during systole does not compromise the stroke volume ejected. In this case the patient's hemodynamic performance is deemed afterload independent. However, increases in afterload are poorly tolerated in patients with no preload reserve (at the top of Frank Starling curve, that is patients that could be fluid overloaded) and/or those patients with left ventricular systolic dysfunction.

Blood pressure is moreover affected by the heart's contractility. The term 'contractility' refers to the inotropic state of the left ventricular myocardium, that is the force and velocity with which the myocardial fibres contract with each heart beat. In clinical practice a variety of contraction-phase indices/parameters such as the velocity of fibre shortening, peak rate of ventricular pressure rise and the end-systolic pressure to volume relationship are in use. The inotropic state of the left ventricle can be changed/supported by the administration of an inotropic drug such as adrenaline. Low contractility and high afterload will reduce stroke volume.

U.S. Pat. No. 6,071,244 and US patent application US 2009/0131805, the entireties of which are herein incorporated by this reference, disclose hemodynamic monitors for determining stroke volume based on arterial blood pressure measurements.

The positive pressure in the thoracic cavity of patients on a respirator can affect the stroke volume of the patient's heart. US patent application US 2009/0131805 discloses that the necessary variations in this pressure can cause considerable variations of stroke volume over a respiratory cycle. US 2009/0131805 recognises that this is particularly the case for hypovolemic patients and proposes to use the degree of variation in stroke volume over a respiratory cycle as an indication of the hemodynamic status.

A major limitation in displaying parameters on screen in a clinical environment, in particular in operating theatres is that the space available for any kind of display is severely limited. At the same time, however, the display has to be fashioned so that the displayed information can be intuitively understood, even if the observer is not close to the display.

SUMMARY OF THE INVENTION

According to an aspect of the present invention there is provided a monitoring device comprising a part for acquiring a signal indicating a level of consciousness, a part for acquiring an arterial blood pressure signal, a display and a processor or processors. The processor or processors are arranged to cause the display to display, for simultaneous viewing, an image showing the blood pressure signal over time, an image showing cardiac output or stroke volume over time, an image showing systemic vascular resistance over time and an image showing the level of consciousness over time based on the signal indicating the level of consciousness. The cardiac output, the stroke volume and the systemic vascular resistance can be determined at least partially based on the arterial blood pressure signal.

The inventors have found a relationship between the depth of anaesthesia/level of consciousness during anaesthesia and the hemodynamic parameters of the patient. Although the strength of this relation was found to vary between patients, lower levels of consciousness were found to be associated with decreased blood flow and pressure. Based on these findings the inventors have realised that simultaneous monitoring of the patient's blood pressure, cardiac output, systemic vascular resistance, blood pressure and fluid responsiveness (by monitoring stroke volume variations or pulse pressure variations in patients on a respirator), while maintaining and limiting anaesthesia depth/the patient's level of consciousness to pre defined targets, should allow finer discrimination and more efficient control of the patient's hemodynamic changes.

The above discussed monitoring device allows simultaneous observation of the level of consciousness of a patient and of the hemodynamic parameters of the patient that can be quantified prior to intubation, namely blood pressure, cardiac output or stroke volume, heart rate and systemic vascular resistance, and to allow the user to correlate changes in these parameters to changes in the patient's level of consciousness by observing the display. This is particularly useful during the induction phase of sedation/anaesthesia, during which, as discussed above, drastic changes in the hemodynamic parameters can occur.

The display for simultaneous viewing can, for example, be such that the above mentioned images are the only images that displayed on the display. A display of this nature is advantageous as it permits the displayed images to be as large as the size of the display area or of a part of the display area allocated for the display of the above mentioned parameters, thereby aiding in guiding an observer to the relevant displayed information. An arrangement of this nature also helps in keeping the required size of a display small, therefore saving valuable space in the operating theatre. Displaying numbers alongside such images can help in quickly ascertaining a current value of a parameter that may also be displayed in the form of an image or another parameter that may not be displayed in the form of images. The images may occupy a majority, for example more than 70% or more than 80% of the available/allocated display area.

The present invention is, however, not limited to monitoring devices that only display the above mentioned images. If it is acceptable to use a larger size display as part of the monitoring device, or if it is acceptable to display the images in a smaller format, then other images (or, more generally, items) can be displayed on the display. In this case the display of the images should nevertheless be such that information displayed to the observer is readily accessible to the observer through its presentation. This can be achieved by grouping the above mentioned images together, so that observer is not disturbed/distracted by other information that may be provided between the images. Put in other words, the images can be displayed in a contiguous fashion/by placing them in contiguous display panels. Some of the images can of course be superimposed over each other, as long as the aim of presenting the images for simultaneous viewing is still fulfilled. The display panels may also comprise components presented in number format, where the display of such components aids the observer in assessing the displayed images. The above mentioned display of current values of parameters in number format is one example of this.

According to another aspect of the present invention there is provided a monitoring device comprising a part for acquiring a signal indicating a level of consciousness, a part for acquiring an arterial blood pressure signal, a display and a processor or processors. The processor or processors are arranged to cause the display to display, for simultaneous viewing, an image showing the blood pressure signal over time, an image showing cardiac output or stroke volume over time, an image showing systemic vascular resistance over time and either, in one operating mode, an image showing the level of consciousness over time based on the signal indicating the level of consciousness, or, in another operating mode, an image showing a variation in stroke volume, a variation in pulse pressure (systolic—diastolic arterial pressure) and/or a pleth variability (pulse oximeter waveform amplitude) index. The cardiac output, the stroke volume, the systemic vascular resistance, stroke volume variation and pulse pressure variation can be determined at least partially based on the arterial blood pressure signal.

The monitoring device may, instead of or in addition to providing a function for switching between a display of the level of consciousness and the display of a variation in stroke volume or pulse pressure may provide a simultaneous display of the level of consciousness and the display of a variation in stroke volume or pulse pressure or pleth variability index, if the available screen size allows such a display. In either case the monitoring device allows observing the level of hydration of the patient (by observing stroke volume and/or pulse pressure variations, or pleth variability index) as well as the level of consciousness, either simultaneously, or through the simple activation of a toggle switch that may be provided on the monitoring device, for example in the form of an icon displayed on a touch sensitive screen. This monitoring device is particularly advantageous post intubation, when meaningful data on stroke volume variation and/or pulse pressure variation or the pleth variability index are available.

It has been recognised that the replacing of a displayed images with an image showing the patient's response to an intervention can provide further useful information to the clinician. To facilitate such a display the processor can be further arranged to, in an operating mode other, than the above described operating modes, replace the display of one of the said images with the display of an image showing a response of a hemodynamic parameter to an intervention. The image showing the response may provide a display of a percentage change in the parameter, relative to the level of the parameter immediately prior to the intervention. The image may display a change in cardiac output, stroke volume, systemic vascular resistance or systolic or mean arterial blood pressure. The processor may be arranged to retain the image showing the absolute values of systolic or mean arterial blood pressure over time and/or an indication of the patient's heart rate on the display.

Either of the above discussed displays avoids a need for clinicians to observe different monitoring devices and/or a need to change between different displays of a particular monitoring device. This is advantageous because the sole/isolated monitoring of blood pressure does not allow identification of determinants of a pressure drop and of their relative contributions to a blood pressure change. The monitoring device of the present invention is thus more user friendly than other monitoring devices. It will be appreciated that this can be of critical importance as it reduces a need for clinicians to alter parameters displayed on the monitoring device while dealing with potentially critical situations.

The inventors have moreover found that, as the patients' hemodynamic response to anaesthesia is complex and individual to the patient and cannot be fully understood by blood pressure monitoring alone, it is inadvisable for a standard protocol aimed at restoring blood pressure and/or blood flow to be followed. Instead therapeutic approaches to the restoration of the patient's blood pressure and/or blood flow and/or oxygen delivery should be informed approaches, targeted to eliminate or at least reduce factors limiting the restoration in the patient's blood pressure and/or blood flow. Any such approaches may be staged, so that different factors are addressed one at a time and/or in a gradual fashion. If a clinician determines, for example based on the display of systemic vascular resistance, that the patient's systemic vascular resistance or the patient's afterload impedes cardiac output, then the clinician may decide to administer a vasodilator that causes a reduction in arterial tone. The effects of the administration of such a vasodilator can be observed through the display of the patient's hemodynamic parameters on the display. Alternative or additional interventions can be undertaken if the administration of the vasodilator is noted as being ineffective or insufficiently effective. Vasodilators may alternatively be used to cause a decrease in venous tone to reduce preload and, as a possible consequence, stroke volume. The net effect of such use of vasodilators is the resultant balance between the reduction in afterload, systemic vascular resistance and preload and can be observed using either of the above discussed monitoring devices. If such observation shows that a reduction in arterial tone is effective in improving the patient's hemodynamic parameters, then such a reduction in arterial tone may be further promoted by the clinician, for example through the administration of arterial vasodilator. If venous vasodilation predominates then a drug having emphasised venous tone effects may be more suitable. If another observation suggests that arterial vasoconstriction may be desirable, for example for increasing blood pressure by increasing arterial tone, then the choice of the type of vasoconstrictor to be administered may be important as some vasoconstrictors may have a more pronounced effect on the arterial, rather than venous tone. Inotropes may be administered to increase ventricular muscle contractility.

It will be appreciated that the aim of restoring blood pressure and blood flow is to ensure that the patient's tissue is sufficiently oxygenated. In addition to the amount of blood reaching the tissue and the ease with which the blood flow reaches the tissue a factor determining oxygenation is the amount of saturated haemoglobin available in the blood for oxygen delivery. If blood haemoglobin values are low, then it will likely be desirable for blood flow to be increased. It will be appreciated therefore that knowledge of blood haemoglobin levels, and of the degree of saturation of the haemoglobin in the blood, is advantageous. The monitoring device may comprise an input for inputting an indication of the blood haemoglobin level, of the saturation of the available haemoglobin and/or of the blood oxygen content for this purpose, for example in the form of a graphical user interface allowing the entry of the relevant values, or in the form of a input arranged to receive a signal representative of any such values from another measurement device. The processor may be arranged to increase a target value for blood flow to account for low blood haemoglobin levels or for a change in haemoglobin and/or saturation levels from a haemoglobin/saturation level at the start of monitoring or at the start of a surgical procedure or a target value.

The inventors have found that restoring normovolemia and ensuring adequate, but not excessive, anaesthesia is a big step towards better control of the patient's blood pressure/hemodynamic status during surgery. The monitoring device of the present invention is suitable for aiding clinicians in this dual aim. It was also found that being able to identify those parameters of the hemodynamic parameters and the level of consciousness that should not be manipulated to restore adequate blood pressure or blood flow or that, even if manipulated, will not lead to an improvement in blood pressure or blood flow is advantageous as the identification of such parameters can prevent the administering of a fluid challenge or drugs that would fail to remedy a reduction in blood pressure in an efficient or effective manner or that may even be detrimental to the state of the patient. It can, for example be envisaged that a patient's systemic vascular resistance has not changed significantly over the course of anaesthetic induction. Any decrease in blood pressure is thus likely to be caused by a decreased cardiac output. This suggests that drugs increasing systemic vascular resistance are contraindicated, as they are likely to increase afterload and may decrease blood flow further without appreciable positive effect.

The monitoring device of the present invention can aid clinicians in identifying likely causes of a reduction in blood pressure and in identifying associated suitable remedies for such reductions as well as unsuitable ways of seeking to remedy such reductions. The monitoring device of the present invention thus affords anaesthetists fuller control of the depth of anaesthesia/level of consciousness and fluid status of the patient.

The monitoring device of the present invention can facilitate identification and possibly even quantification of the drivers behind changes in blood pressure during anaesthetic induction by displaying the above discussed parameters. The monitoring device of the present invention can further facilitate monitoring the efficiency of measures taken by clinicians to correct blood pressure (and level of consciousness) to target levels by displaying such target levels. Such target values may, for example, correspond to, or close to the values the hemodynamic parameters or blood pressure had pre-induction. If, for example, a patient is assessed to have sufficient blood flow prior to a (surgical) intervention, then this level of blood flow may be used as a good blood flow target if the patient's blood oxygen content level remains unchanged. The use of target values that are based on pre-induction levels of blood pressure or of a hemodynamic parameter allows the use of the monitoring device for displaying relative change, without a need to calibrate the monitoring device for the display of absolute values.

Alternatively any such target values may be predetermined values. The use of predetermined values can be particularly advantageous in situations where the pre-induction values are unsuitable target values, for example for patients that are normally hypertensive. Providing target values for blood pressure and cardiac output is particularly advantageous and the monitoring device may be arranged to provide target values for blood pressure and cardiac output.

Optimising blood flow parameters during surgery in an informed/targeted fashion has been shown to improve the outcome of surgery. It has in particular been shown that the side effects suffered by patients following surgery can be reduced. Consequently the length patients have to stay in hospital post surgery can also be reduced.

The signal indicating the level of consciousness may be a biopotential signal or based on a biopotential signals. The biopotential signals can, for example, be EEG signals that can be used as the basis for determining the indication of the level of consciousness of the patient from which the biopotential signals have been derived. The monitoring device may comprise a means for determining a level of consciousness from the biopotential signals. Alternatively, the signal indicating a level of consciousness may be received from a device provided outside of the monitoring device. The signal may thus be an output signal of a device that determines the level of consciousness, for example based on the above mentioned biopotential signals. Such an output signal may, for example, be a bispectral index signal. In this case the part for acquiring a signal indicating a level of consciousness of the monitoring device may be a simple input (connector) arranged to receive a connection/cable or wireless transmission from the device that determines the level of consciousness. One suitable external device for determining the level of consciousness is Covidien's Bispectral Index® device (Covidien plc, Cherrywood Business Park, Loughlinstown, Co. Dublin, Ireland). Another such device is the SEDline Brain Function Monitor (SEDline, Irvine, Calif., USA). The part for acquiring a signal indicating a level of consciousness may also comprise an analogue to digital converter, if any signal received from an external device is an analogue signal.

The processor(s) may further be arranged to display a target level for the depth of anaesthesia/level of consciousness and/or to provide an indication of whether or not the level of consciousness/depth of anaesthesia is within a predetermined range. This predetermined range may be a range that is known as indicating a level of consciousness that prevents post surgical recall/awareness, while not being lower than necessary for the purpose of preventing post surgical recall. If the level of consciousness/depth of anaesthesia is measured using bispectral index, an appropriate range can be between 40 and 60.

U.S. Pat. No. 6,071,244, US patent publication number US 2009/0131805 and co-pending UK patent application no. 1002331.5 disclose methods of determining the left ventricular stroke volume of a patient based on the patient's arterial blood pressure. The documents and the methods disclosed therein are incorporated expressly herein by this reference and can be used for determining a stroke volume for display in embodiments of the present invention. Cardiac output can be calculated as the product of stroke volume and heart rate. The heart rate itself can be directly derived from the arterial blood pressure signal or, alternatively, can be provided via an external input of the monitoring device, for example from an ECG apparatus. The mean arterial pressure can also be directly derived form the arterial blood pressure signal in known ways. Systemic vascular resistance can then be calculated as the ratio of mean arterial pressure and cardiac output.

Changes in stroke volume may be monitored over a number of heart beats, for example so that the changes in stroke volume over one or more respiratory cycles can be evaluated. It is normal for stroke volume to vary over a respiratory cycle of a ventilated patient because the thoracic pressure of the patient changes. Large variations in stroke volume can indicate that the patient is hypovolemic. A display of changes in stroke volume can thus aid clinicians in determining whether or not a patient is hypovolemic. The patient's hydration status can also be determined by measuring the patient's pleth variability index. A suitable device for determining this index is the Masimo Rainbow SET SpHb total haemoglobin measurement (Masimo, Irvine, Calif.).

The part for acquiring the arterial blood pressure signal may generate the arterial blood pressure signal based on a signal received from a sensor or may include the sensor itself. Alternatively the part for acquiring the arterial blood pressure signal may be an input for receiving a signal from a device that generates such a signal. One device suitable for this purpose are the invasive arterial pressure monitoring systems available from LiDCO Ltd. of 16 Orsman Road, London, N1 5QJ, UK, such as the LiDCOrapid or LiDCO™ plus hemodynamic monitors.

The processor(s) may, in addition to causing the display to display images of the above mentioned parameters, display a current value of one or more of the parameters that are being displayed in the form of images, alongside the corresponding image. This further clarifies the display. It is particularly envisaged that the current value of the level of consciousness of the patient is displayed alongside the image of the stroke volume variation or pulse pressure variation or pleth variability index if the monitoring is arranged to toggle between displaying an image of the level of consciousness and an image of the stroke volume or pulse pressure variation or pleth variability index.

It is moreover envisaged that present and past values of the level of consciousness, in arrangement where it is not displayed in the form of a separate image, are superimposed in number format over one of the images displayed on the display. The past and present values of the level of consciousness can advantageously be displayed at the correct time point/the time point at which they occurred, so that the indication of the level of consciousness is provided alongside a substantially simultaneously acquired/determined hemodynamic parameter.

This has been recognised as being advantageous sin its own right and according to another aspect of the present invention there is provided a monitoring device comprising a part for acquiring a signal indicating a level of consciousness, a part for acquiring an arterial blood pressure signal, a display and a processor or processors. The processor or processors are arranged to cause the display to display one or more of an image showing the blood pressure signal over time, an image showing cardiac output or stroke volume over time and an image showing systemic vascular resistance over time. The processor or processors are moreover arranged to cause the display to display values of the level of consciousness in number format superimposed over a said displayed image, at time points in the image at which the values of the level of consciousness had occurred.

The displayed images may plot the level of consciousness or the above discussed hemodynamic parameters over time. The images may be displayed so as to be time synchronised with each other. A display of this nature enables the user to detect simultaneous changes in the level of consciousness and in one or more hemodynamic parameters more easily. An identification of any such simultaneous changes may help in identifying the cause for the changes and in determining an appropriate way of countering any undesired changes more reliably and quickly.

A display of the change in stroke volume may be a display of the percentage change of stroke volume over a period of time. Such a display can be in number format. The change in stroke volume can alternatively or additionally be displayed in the form of a curve plotting stroke volume one a per beat basis over time. A range of stroke volume values centred on the mean stroke volume and indicating upper and/or lower threshold beyond which a variation in stroke volume is indicative of a hypovolemic state of the patient may further be superimposed over any such curve for easy visualisation of excessive variations in stroke volume.

The operation of the processor may be based on software code stored in the monitoring device.

The monitoring device may further comprise a memory for storing one or more of the signal indicating a level of consciousness, the indication of the level of consciousness, the arterial blood pressure signals and a one or more of the above mentioned hemodynamic parameter that may be derived from the blood pressure signal. Storage of one or more of these parameters is useful for patient care, for example for a post operative review of the anaesthetic procedure and/or the hemodynamic condition of the patient.

Storage of these values can moreover permit analysing any correlation between the stored values and the monitoring device can be arranged to analyse stored data values to identify any such correlation. The monitoring device may be arranged to display an identification of any such correlation on the display. Identified correlations can be useful for predicting any future changes in the hemodynamic parameters of the patient. The monitoring device may, for this purpose, display on the display a value indicating a change or improvement that is likely to be achieved if a hemodynamic parameter or the level of consciousness is changed by a given amount. This can provide a prediction of a change in systolic or mean arterial blood pressure that is likely achievable from one or more of a change in the level of consciousness of the patient, a change in cardiac output, a change in stroke volume, a change in heart rate and a change in systemic vascular resistance. Such a prediction can be obtained by interpolating between previously obtained values. For example, the fitting of a characteristic curve to previously, obtained pairs of values of the level of consciousness of a particular patient and of the systolic or mean arterial blood pressure of the patient may provide an indication of the increase in systolic or mean arterial blood pressure that can be achieved by increasing the level of consciousness of the patient by an amount chosen by a clinician. If, for example, a linear function can be fitted/is fitted to stored values, then the slope of this function may be displayed (in number format and/or by displaying the curve with the correct slope) to provide the clinician with an indication of potentially achievable gains A linear function may for example be fitted to a series of data sets comprising values indicative of the patient's level of consciousness and blood pressure values. Displaying the slope of this function can inform the clinician of a likely increase in blood pressure that would be achieved by increasing the level of consciousness by a predetermined value, such as a unit value. The monitoring device may thus provide the clinician with information of a likely achievable increase in systolic or mean arterial blood pressure if an amount of anaesthetic agent that is administered to the patient is reduced. This is particularly useful in cases where a current level of consciousness is lower than is required for the purpose of the procedure the patient is subjected to. An increase in systolic or mean arterial blood pressure value achieved or achievable in this way/by increasing the level of consciousness of the patient to a level that, while higher than a current level, is still sufficiently low to be suitable for the procedure/operation the patient is being subjected to may be such that further intervention may not be required and can therefore be avoided.

It will be appreciated that, if the dependence of blood pressure or another hemodynamic parameter on the level of consciousness of the patient is strong (that is if the above mentioned slope is steep), then changes in the level of consciousness will likely affect blood pressure or the other hemodynamic parameters strongly. In this case it is advantageous for the level of consciousness to be displayed more prominently on by the monitoring device. The processor(s) may therefore be arranged to display the level of consciousness in a more prominent manner if the slope (or its absolute value) exceeds a predetermined threshold. The processor(s) may for example cause a display of an image of the level of consciousness over time instead of only a number indicating the current level of consciousness in this case, or suggest changing the display in this manner to the user.

The memory may be provided internally of the monitoring device and/or in the form of a removable memory. Such a removable memory may be provided in the form of a card for receipt in a receptacle of the monitor. A card of this nature can be patient specific so that it may be kept with the patient's file once it is no longer needed for monitoring the patient.

Recording a series of data sets and using the recorded data sets to provide a curve characteristic for the patient has been recognised as being advantageous in its own right. According to another aspect of the present invention there is provided a monitoring device comprising a part for acquiring a signal indicating a level of consciousness, a part for acquiring an arterial blood pressure signal a display and a processor or processors arranged to record a series of data sets over a period of time. Each data set comprises at least a value of the signal indicating a level of consciousness at a time point and one or more of a value of the arterial blood pressure signal at the time point and a hemodynamic parameter or hemodynamic parameters determined based on the blood pressure signal. The processor or processors are further arranged to determine, based on the series of data sets, a characteristic of one or more of a change in mean or systolic arterial blood pressure, in systemic vascular resistance, in cardiac output, in stroke volume, in stroke volume variation and in pulse pressure variation dependent on the level of consciousness.

The processor or processors can further be arranged to cause the display to display one or more of the characteristics and an indication of a change in blood pressure that is to be expected, based on the characteristics, for a unit change in the displayed level of consciousness.

The monitoring device may further be arranged to time stamp the arterial blood pressure signal and/or the signal indicating a level of consciousness. Using time stamped signals allows collating signals obtained or received substantially simultaneously in data sets. The monitoring device may be arranged to interpolate between the data sets, for example by fitting a mathematical function to a series of data sets. The series of data sets can span one or more of a range of states of consciousness, a range of systolic or mean arterial blood pressure values, a range of stroke volume values, a range of heart rates, a range of systemic vascular resistance values and a range of cardiac output values. The processor(s) can be arranged to use the mathematical function, once fitted, as the characteristic curve of the patient from which the data has been obtained. The processor(s) can derive predictions of a change in hemodynamic parameters and/or in the systolic or mean arterial blood pressure that can likely be achieved by altering one or more of the level of consciousness of the patient or one or more of the hemodynamic parameters. The processor(s) can, for example derive predictions of a likely change in systolic or mean arterial blood pressure achievable by an induced change in the systemic vascular resistance, cardiac output and/or level of consciousness. The mathematical function fitted may be a linear function.

The monitoring device may enable a user to input the occurrence of an event, such as, for example, the beginning of the induction of sedation/anaesthesia, the beginning of ventilation, the start of a surgical procedure or a time point at which a drug or fluid challenge is administered. The processor(s) may be arranged to display markers on an image displayed by the display, indicating the correct time point of the event alongside or superimposed over data in the images. The monitoring device may comprise an input means that allows the user to indicate to the monitoring device that a relevant event has occurred. Such an input means may be arranged to also enable the user to specify the nature of the event.

The processor may moreover be arranged to display two images of any (or all) of the above mentioned parameters, wherein one of the two images displays the change/trend in the parameter over one (longer) time period/axis, while the other image displays the change/trend in the parameter over a shorter time period. A display of this nature facilitates the identification of long term trends in changes in the parameter in the first image as well as a more detailed analysis of more recent or acute changes in the second image. It is, for example, envisaged that the processor can be arranged to provide a long term display of one or more of systolic or mean arterial blood pressure, heart rate and stroke volume alongside a corresponding shorter term display of the corresponding parameter or parameters.

While the present invention has been described with reference to a monitoring device, the present invention is not limited thereto. The present invention also extends to methods of monitoring a patient as well as methods of training to monitor a patient. According to another aspect of the present invention there is provided a method of monitoring anaesthetic induction comprising recording a series of data sets over a period of time. Each data set comprises a value of a signal indicating a level of consciousness of a patient or simulated patient applicable at a time point and a value of said arterial blood pressure signal applicable at the time.

The period of time includes a period of time prior to the administration of an anaesthetic and/or sedative, a period of time between the administration of the anaesthetic and/or sedative and intubation and a post intubation period.

According to another aspect of the present invention there is provided a method of restoring blood pressure or blood flow of a patient or of training to restore the blood pressure of a simulated patient following the induction of anaesthesia and/or sedation. The method comprises correcting a deviation in the level of consciousness of the patient or simulated patient during anaesthetic induction from a desired level. This correction may improve the patient's blood pressure. If any such improvement is insufficient, the hydration level of the patient or simulated patient is considered and one or more fluid challenges are administered, if the patient is determined to be hypovolemic. If the patient's or simulated patient's blood flow or blood pressure remains below a desired target, a suitable drug is determined by administering potentially suitable drugs in a staged manner.

According to another aspect of the present invention there is provided a method of restoring blood pressure or blood flow of a patient or of training to restore the blood pressure of a simulated patient following the induction of anaesthesia and/or sedation. The method comprises adjusting the administration of anaesthetic or sedative to the patient or simulated patient so that the patient's or simulated patient's level of consciousness is within a predetermined range, determining if the patient is hypovolemic and administering one or more fluid challenges if the patient is determined to be hypovolemic. The method comprises further determining if the patient's or simulated patient's systolic or mean arterial blood pressure has reached a desired value and, if the patient's systolic or mean arterial blood pressure has not reached the desired value determining, through staged application, whether a vasopressor acting predominantly on the venous part of the patient's or simulated patient's vascular system, a vasopressor acting predominantly on the arterial part of the patient's or simulated patient's vascular system and/or an inotropic drug is suitable for increasing the patient's or simulated patient's blood pressure and/or blood flow.

According to another aspect of the present invention there is provided a method of restoring blood pressure and/or blood flow of a patient or of training to restore the blood pressure and/or blood flow of a simulated patient following the induction of anaesthesia and/or sedation. The method comprises displaying on a display an image showing a development in the patient's or simulated patient's blood pressure level and of the patient's or simulated patient's level over consciousness over time and adjusting an amount of anaesthetic and/or sedative administered to the patient or to the simulated patient until the level of consciousness of the patient is within a predetermined target zone. Following intubation an image showing a development in the patient's or simulated patient's blood pressure level over time and an image of a variation in the patient's or simulated patients left ventricular stroke volume and/or in the patient's or simulated patients pulse pressure and/or in the patient's or simulated patients pleth variability index is displayed on the display. It is then decided, based on the image of the variation in left ventricular stroke volume, pulse pressure and/or pleth variability index whether or not the patient is likely to be hypovolemic and, if so, administering a fluid challenge, if a current blood pressure has not reached a desired value. An image of a change in the patient's or the simulated patient's stroke volume over time is displayed following an administration of the said fluid challenge. It is then determined if the patient's or the simulated patient's blood pressure has reached the desired value and, if the patient's or the simulated patient's blood pressure has not reached the desired value, a drug that is suitable to increase the patient's or simulated patient's blood pressure is determined, through the staged application of various drugs that could be suitable. Drugs having a shorter term effect may be applied before drugs having a longer term effect, to avoid superimposing the effects of two drugs and thereby rendering attributing a change in the patient's condition to a particular drug difficult.

A marker may be set at the time of an intervention. Based on the position of the marker in displayed image, it can be decided whether or not the intervention has affected the observed change in systolic or mean arterial blood pressure or blood flow.

BRIEF DESCRIPTION OF THE DRAWINGS

Embodiments of the present invention will be described in the following by way of example only and with reference to the accompanying drawings, in which.

DETAILED DESCRIPTION OF EMBODIMENTS

Figure 1:
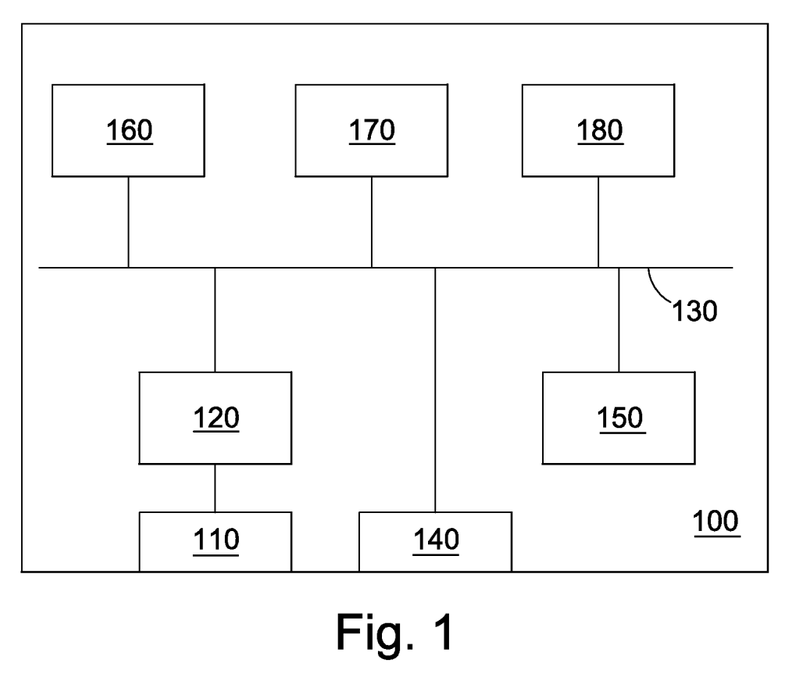
FIG. 1 shows an architecture of a hemodynamic monitor of an embodiment.

An embodiment of the present invention will be described in the following. FIG. 1 shows an overview of a monitor 100 of an embodiment of the present invention. The monitor 100 comprises an input port 110 to which a device providing an analogue pressure waveform can be connected and through which the analogue pressure waveform can be input into the monitor 100. An analogue to digital converter 120 is provided for converting any analogue pressure waveform received through the input port 110 into a digital signal. The digital signal can be placed on the bus 130 for further processing. The monitor 100 further comprises a second input port 140 to which a device providing a BIS signal can be connected and through which the BIS signal can be input into the monitor 100. In the present case the BIS signal is assumed to be a digital signal, so that it can be used directly by the monitor 100 without prior analogue to digital conversion. It will, however, be appreciated that other arrangements, in which an analogue to digital converter is used for converting an analogue signal indicative of a patient's level of consciousness prior to supplying this signal to the bus 130, are also contemplated. The monitor 100 further comprises a microprocessor 150, a RAM 160, which may act as buffer, permanent storage means provided in the form of a hard drive 170 and some input/output means 180. Examples of such input/output means are monitors, printers and keyboards etc. Although not shown, the monitor 100 may further comprise input means through which a signal indicative of the heart rate of the patient may be received.

The results of a study conducted at Kings College Hospital, London, UK are discussed in the following. The purpose of the study was to quantify the changes occurring across anaesthetic induction in arterial pressure, cardiac output and systemic vascular resistance from their pre-induction baseline level in peripheral vascular surgery patients. The correlation of these hemodynamic changes with post induction preload responsiveness parameters and the change in depth of anaesthesia was also explored.

Forty-six adult patients (36 male, 10 female) with ASA grades between 2 or 4 (94% grade 3 to 4) undergoing complex peripheral vascular surgery (mean duration 4.1 hours) with an average age of 73 years (range 46-92) were studied. Anaesthetic induction was with remifentanil and propofol target controlled infusion (TCI). Changes of hemodynamic data from the pre-induction baseline to immediately post intubation were recorded from analysis of the peripheral artery pressure waveform using the LiDCO hemodynamic monitor (LIDCO Ltd., UK). Changes of depth of anaesthesia from the pre-induction baseline to immediately post intubation were recorded from the patients' foreheads (BIS from Covidien). One minute average changes in hemodynamic and BIS results were compared.

The average fall in mean arterial pressure was −40%±12% (range −13% to −62%). This fall was predominantly driven by a reduction in cardiac output fall of −33%±14% (range: +15 to −58%) and a lesser average reduction in systemic vascular resistance of −6%±18% (range: +31 to −36%). On average the reduction in cardiac output contributed 82% of the pressure fall and only increased in one out of the 46 patients. Systemic vascular resistance in contrast fell in 28 out of the 46 patients and was unchanged or rose in 18 out of the 46. The fall in cardiac output reflected a 28% reduction in stroke volume (±15%; range: +10 to −63%) plus a much smaller reduction of −7% (±13%; range: 34 to −37%) in the average heart rate.

The average stroke volume variation SW % immediately post induction and intubation was 17%. 16 patients (35%) were not fluid responsive (with the stroke volume variation being less than 10%; SVV %<10%). 20 patients (44%) were fluid responsive (with the stroke volume variation being greater than or equal to 10%; SVV % ≥10%). Ten patients suffered from a degree of heart rate variation post intubation that precluded stroke volume based fluid responsiveness evaluation. The reductions in cardiac output and stroke volume fluid responsive patients was significantly greater than in non-responsive subjects (t test SPSS, cardiac output reduction of −36% for fluid responsive patients, compared to a reduction in cardiac output of −24% for fluid non-responsive patients, P<0.001 and a reduction in stroke volume of −31% for fluid responsive patients compared to a reduction in stroke volume of −17% for fluid non responsive patients, P<0.001).

Figure 2:
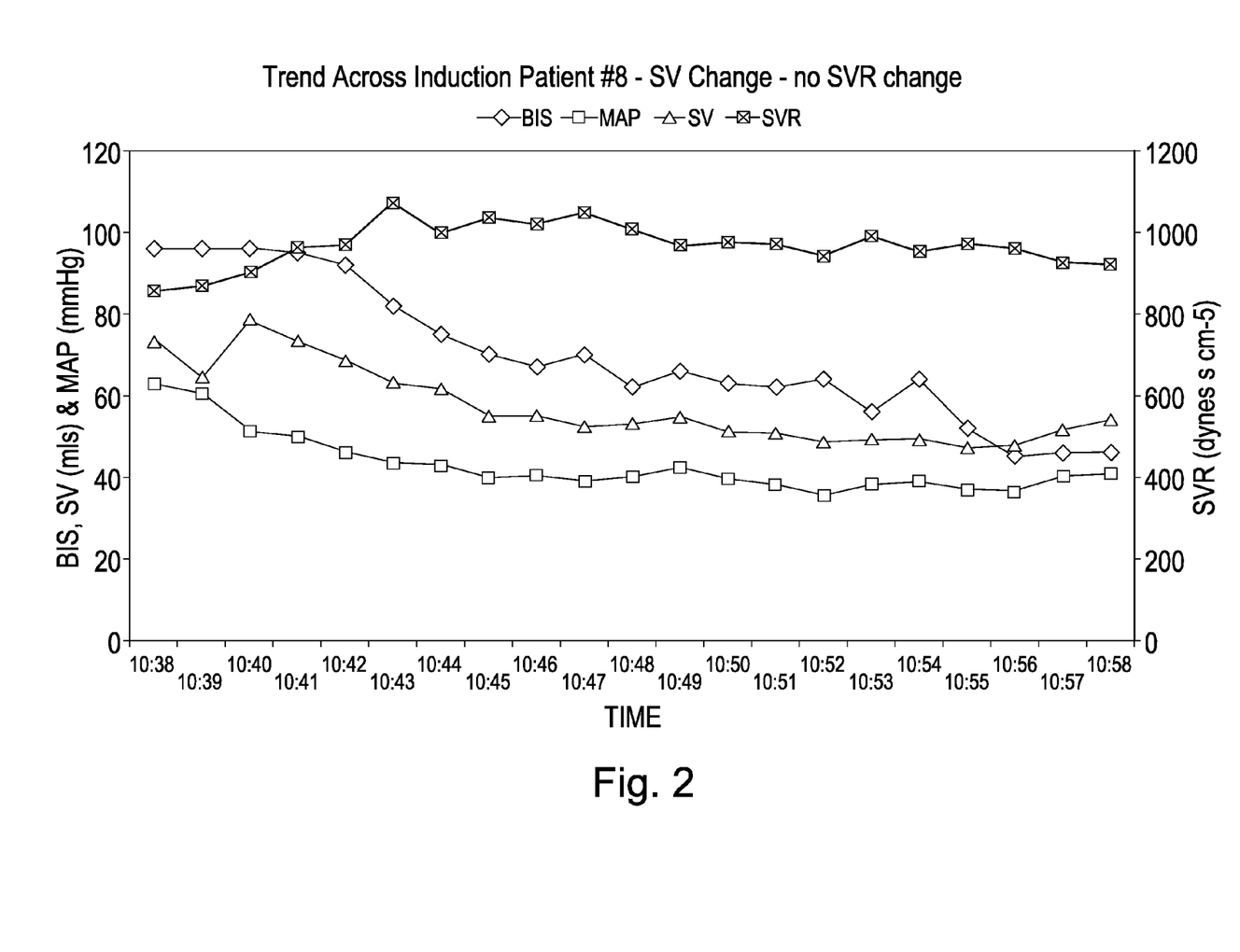
FIG. 2 shows the results of a study in which hemodynamic parameters of a patient and the patient's level of consciousness have been monitored.
Figure 3:
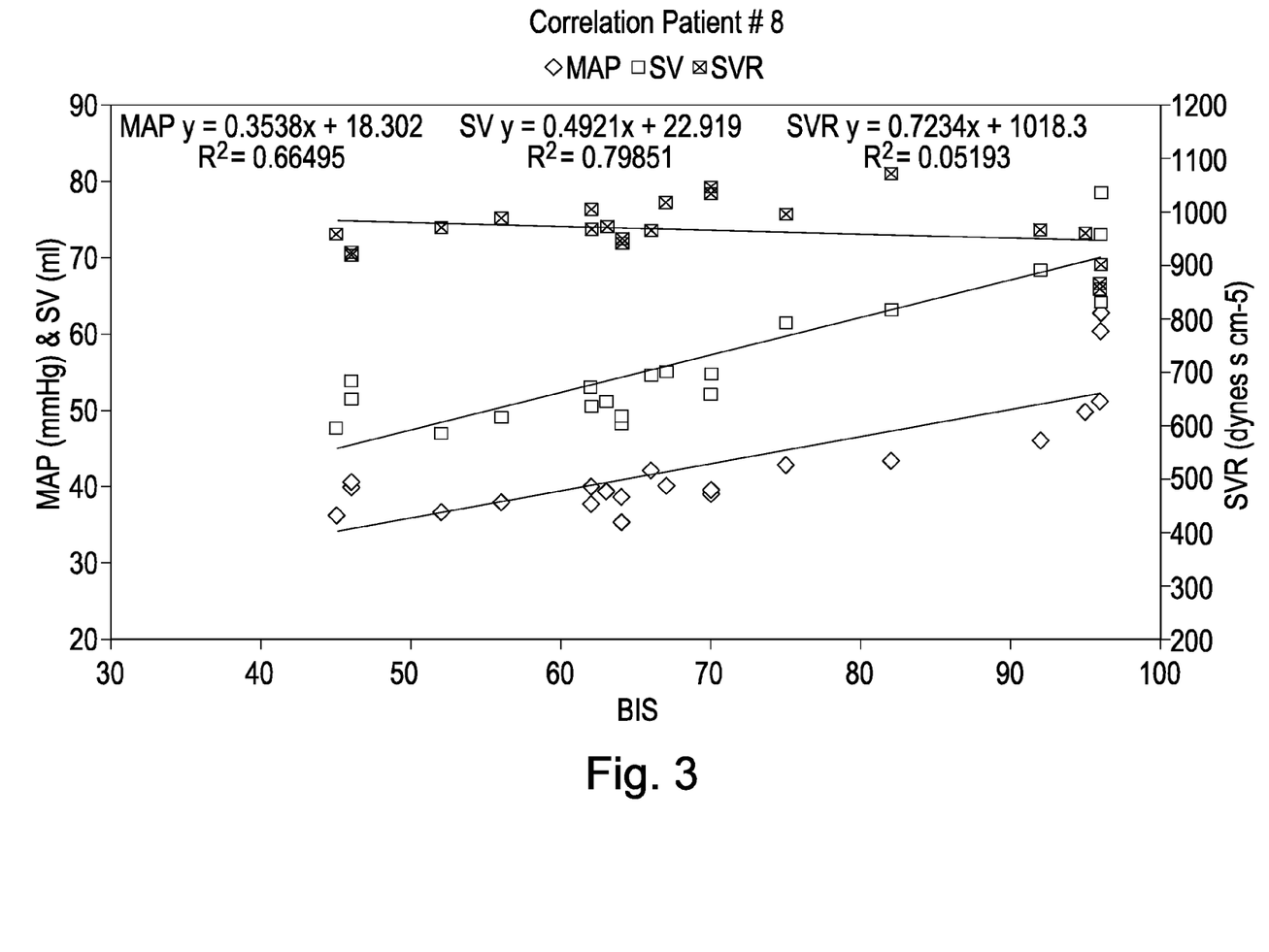
FIG. 3 shows the correlation between monitored hemodynamic parameters and level of consciousness of the study results of FIG. 2.

The average fall in BIS was 58%±11% (range 91.3 to 39.5). For each patient there was a good correlation/linear relationship (Pearson correlation coefficient) between the responding hemodynamic parameter(s) and the absolute BIS value and the percentage change in BIS value. Recorded data for one of the patients are illustrated in FIG. 2. The correlation between BIS and mean arterial pressure, stroke volume and systemic vascular resistance respectively is illustrated in FIG. 3 the data illustrated in FIG. 2. The average reduction, when compared to pre-induction levels, in hemodynamic parameter per unit change in BIS was: Cardiac output 47 ml/min (range 0.11 to −0.01 l/min), mean arterial pressure 0.75 mmHg (range 1.74 to 0.14 mmHg), heart rate 0.108 beats/min (range 0.76 to −0.41 bpm), stroke volume 0.461 ml (range 1.5 to −0.16 ml) and systemic vascular resistance 1.9 dynes s cm$^{-5}$ (range 17.69 to −9.82 dynes s cm$^{-5}$).

The observed correlation between BIS and the hemodynamic parameter(s) means that brain EEG activity level monitoring with BIS, and possibly other EEG monitors/EEG monitors, mirror the time course and are directly proportional to the strength of the effects of the anaesthetic agent(s) on blood pressure/hemodynamics. Excessively low levels of brain activity, as a consequence of too much anaesthesia, are consequently potentially deleterious to the patient as they lower blood pressure and blood flow/oxygen delivery further than is necessary for the purpose of anaesthesia.

The study has indicated that the fall in blood pressure during induction of anaesthesia is partly driven by the patient's fluid status, in particular a reduction in blood flow, and, to a lesser degree, by the patient's level of consciousness/depth of anaesthesia. This reduction in blood flow is mostly due to a reduction in left ventricular stroke volume. Changes in the systemic vascular resistance play a lesser role. The falls seen in cardiac output and stroke volume are significantly worse in the presence of preload responsiveness than in patients that are not fluid responsive. Changes in depth of anaesthesia/level of consciousness, as measured by BIS, correlate well with these hemodynamic changes. Although the slope of a fitted linearly function indicating the relationship between BIS and hemodynamic parameters varies between patients it is clear from the study that allowing higher BIS scores will in general be associated with improvements to both blood flow and pressure. Simultaneous monitoring of blood flow, SVR, blood pressure and fluid responsiveness while maintaining anaesthesia depth to a target should allow finer discrimination and more efficient control of the hemodynamic changes seen consequent to induction.

Figure 4:
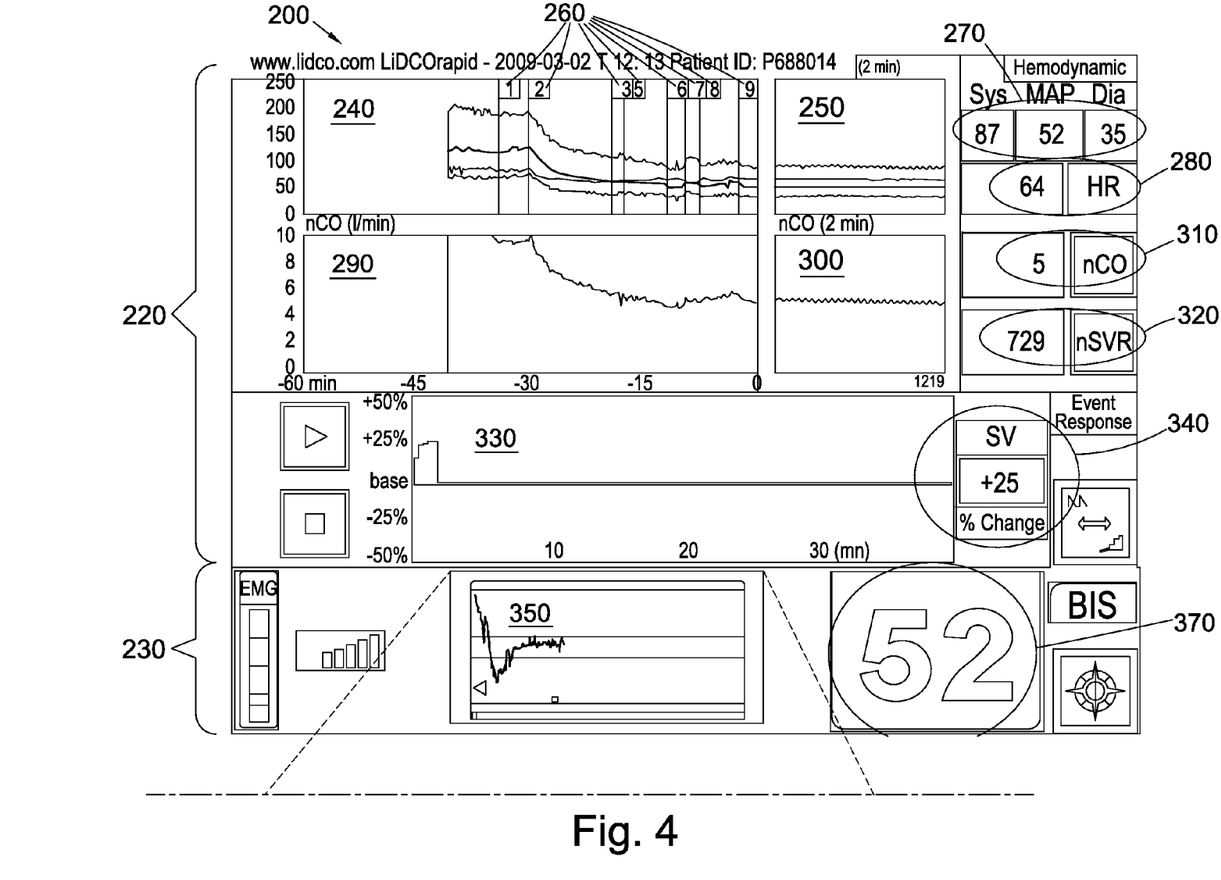
FIG. 4 shows a display of one embodiment.

FIG. 4 shows an example of a display 200 according to one embodiment. The display is a flat panel display comprising two areas 220 and 230. The processor 150 causes the display to display hemodynamic parameters in area 220 and an indication of the level of consciousness, in this case bispectral index, in area 230. Area 220 in turn is divided into an upper, middle and lower panel. The upper panel comprises a display area 240. In this display area 240 the received arterial blood pressure signal is plotted over time, giving rise to the wide band displayed in this area of FIG. 4. Also plotted over time is the patient's mean arterial blood pressure and the patient's heart rate. Both the trace for mean arterial blood pressure and for heart rate are, in this example, superimposed over the band created by the display of the blood pressure signal. These values are displayed over a long time period in display area 240, in this example over 10 minutes, to allow clinicians to observe, at a single glance and without having to manipulate display parameters, any trends or long term changes in the displayed parameters. The time period chosen for the display area 240 can be different from the 10 minute time scale chosen in this example, as long as an appreciation of long term changes and trends is possible. The monitoring device may moreover allow a user to set the time scale for this display window to meet the user's requirements and/or may facilitate automatic scaling of the time scale to the duration of the display.

The processor is further arranged to provide event markers 260 in long term display area 240 to indicate the points in time at which interventions have been conducted. The processor may allow a user to input a description of the nature of the event. The numbering of the event markers 260 in FIG. 4 allows easy identification of the nature of such an event via a list of event description maintained by the monitoring device.

The upper display panel also comprises a shorter term display area 250. The parameters displayed in display area 250 are the same as those displayed in display area 240. However, the time scale chosen for display area 250 is shorter (in this case 2 minutes) than the time scale chosen for display area 240. The amount of detail (resolution) displayed in display area 250 is higher than that displayed in display area 240. The combination of display areas 240 and 250 thus allows observing long term changes in the displayed parameters (though display area 240) and shorter term changes/acute changes (though display area 250). The mean arterial blood pressure as well as the systolic and diastolic blood pressures are moreover displayed in number format in area 270. The heart is moreover displayed in number format in area 280.

The middle panel of area 220 also comprises a long term display area 290 and a short term display area 300 similar to the long and short term display areas 240 and 250 of the upper panel of the area 220. The long and short term display areas 290 and 300, however, plot cardiac output over time. The cardiac output is moreover displayed in number format in area 310 alongside an indication of stroke volume in number format in area 320.

The lower panel of display area 200 is an event response display 330 plotting a change of a hemodynamic parameter, in this case stroke volume, over time since the occurrence or input of an event. This change is in this example plotted as a percentage change of the stroke volume at the time of the event. A current value of this percentage change is also shown in number format in area 340.

The processor causes an indication of the level of consciousness, in this case bispectral index, of the patient to be displayed in display area 350 of area 230. The level of consciousness is plotted over time. A band 360 indicates the range of bispectral index values (from 40 to 60) that is normally clinically accepted as preventing awareness/post surgical recall, while being sufficiently high to minimise side effects of the anaesthetic process. Also provided is a display 370 of the current bispectral index value in number format.

It will be appreciated that, although in FIG. 4 the display 350 is not provided in a time synchronised fashion with displays 240 and 290 (which are time synchronised to each other) or with displays 250 and 300 (which are also time synchronised to each other), time synchronisation of display 350 to one or more of displays 240, 250, 290 and 300 can also be provided. Additionally or alternatively the event markers 260 shown in FIG. 4 may also be provided in the display area 350, so that clinicians can, at one glance and without having to manipulate the display of the monitoring device, link a change evident from the display areas 240 and/or 290 with a change in the level of consciousness, as displayed in area 350.

Figure 5:
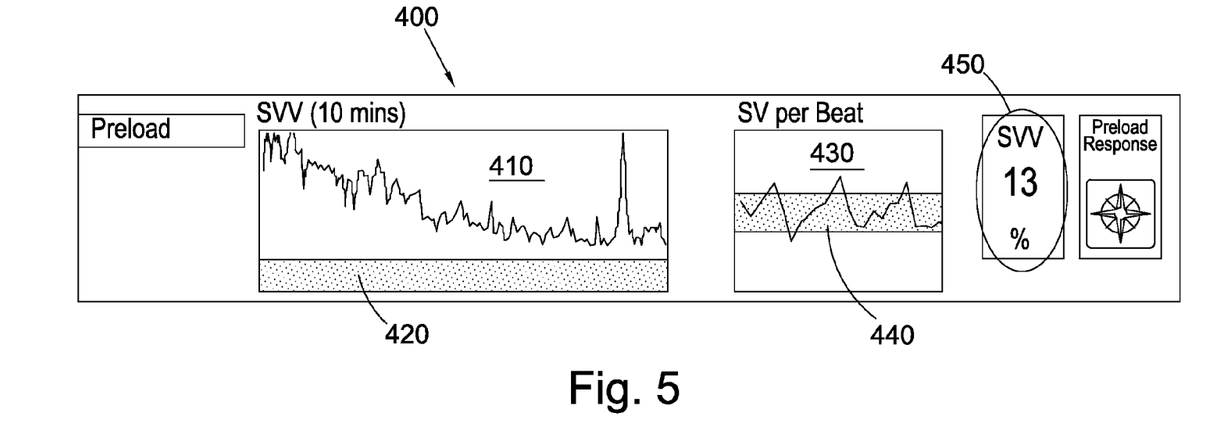
FIG. 5 shows a further display panel that can be included in a display.

FIG. 5 shows a further display panel 400. This further display panel 400 may be displayed alongside the display panels shown in FIG. 4, for example immediately above it or below it, or besides the lower display panel of FIG. 4 that comprises display area 330. Alternatively the display panel 400 may replace one of the upper, middle or lower display panels shown in FIG. 4, for example. The display panel 400 comprises a display area 410 in which a maximum stroke volume variation over a predetermined period of time is plotted over time. The predetermined period of time can be a respiratory cycle, so that display area 410 displays changes in stroke volume over the respiratory cycle. Also displayed in area 410 is a boundary zone 420 for the stroke volume variation. The boundary zone defines the area of 10% variation in stroke volume. Variations in the stroke volume going beyond this area may be considered by the clinician as indicating that the patient is hypovolemic. The time scale of the display area 410 is such that long term changes in stroke volume variation can be observed. It will be appreciated that, although not shown in FIG. 5, event markers similar or equivalent to event markers 260 shown in FIG. 4 may also be displayed. Also provided is a shorter term plot 430 of stroke volume (rather than stroke volume variation) over time. The time scale of plot 430 has been chosen such that variations in stroke volume over a small number of respiratory cycles can be observed. A band 440 indicating 10% variation of the actual stroke volume is also displayed to enable to clinician to form a view on whether or not the patient may be or become hypovolemic. The current stroke volume variation value is also displayed in number format in area 450 alongside area 430.

As mentioned above, it may further be useful for the clinician if an indication of changes that can likely be gained in blood pressure or blood flow with a change in another parameter was available. FIG. 3 provides such an indication. It shows, for example, that mean arterial blood pressure (MAP) and stroke volume (SV) are directly proportional to the bispectral index. FIG. 3 thus intuitively shows that in situations where a patient's level of consciousness has been lowered below a level needed to prevent awareness/post surgical recall, a reduction in the amount of anaesthetic or sedative administered to the patient can bring about an improvement in mean arterial blood pressure and/or stroke volume. FIG. 3 also indicates that a change in the level of consciousness of the patient is unlikely to bring about a change in systemic vascular resistance. It will be appreciated that indications of this nature can be clinically useful, although a decision on how blood pressure and flow should or could be raised to a desired level lies of course entirely with the clinician. It is thus envisaged that one or more of the fitted curves shown in FIG. 3 may be displayed on the display of the monitoring device. The display of fitted curves other than those shown in FIG. 3 is also envisaged. Additionally or alternatively the slope of the fitted curve(s) can be displayed in number format (expressed for example in mmHg/BIS unit for MAP or in ml/BIS unit for stroke volume) to give clinicians an indication of a likely change brought about by an induced change in the level of consciousness of the patient or simulated patients.

It will be appreciated that the present invention is not limited to the embodiments described above. It is moreover envisaged that different ways of displaying a level of consciousness and the patient's hemodynamic parameters may be used during different stages of anaesthetic induction. In the induction phase, for example, up until the intubation of the patient, the processor may cause the display to display blood pressure, the drivers of changes in blood pressure, cardiac output and systemic vascular resistance and the level of consciousness of the patient. These displays can be superimposed over each other to provide a compact display. Alternatively, these displays can be separately provided in three panels so allow easy analysis of the displayed data. Following intubation the processor may cause the display to change (for example after user input of an event indicating the completion of intubation), for example to the display shown in FIG. 4, to allow an easy and quick analysis of the changes in the hemodynamic parameters of the patient alongside the changes in the level of consciousness. It is particularly envisaged that a display of this nature and for this purpose should comprise a plot of blood pressure, cardiac output, means arterial pressure or systolic pressure and the level of consciousness over time.

Following an analysis of the reasons for a drop in arterial blood pressure during anaesthetic induction, an anaesthetist will likely be interested in addressing any identified reasons for such a drop. The processor can be arranged to aid the anaesthetist's attempts to reverse this trend by displaying those hemodynamic parameter useful for observing the patient's reactions to any steps taken by the anaesthetist. As discussed above, a plot of a variation of stroke volume over time or of stroke volume variation over time (as, for example, shown in FIG. 5) can be useful for identifying a hypovolemic state of the patient. In one embodiment a plots of blood pressure, heart rate, cardiac output and systemic vascular resistance is further provided alongside a plot of the level of consciousness of the patient over time.

Figure 6:
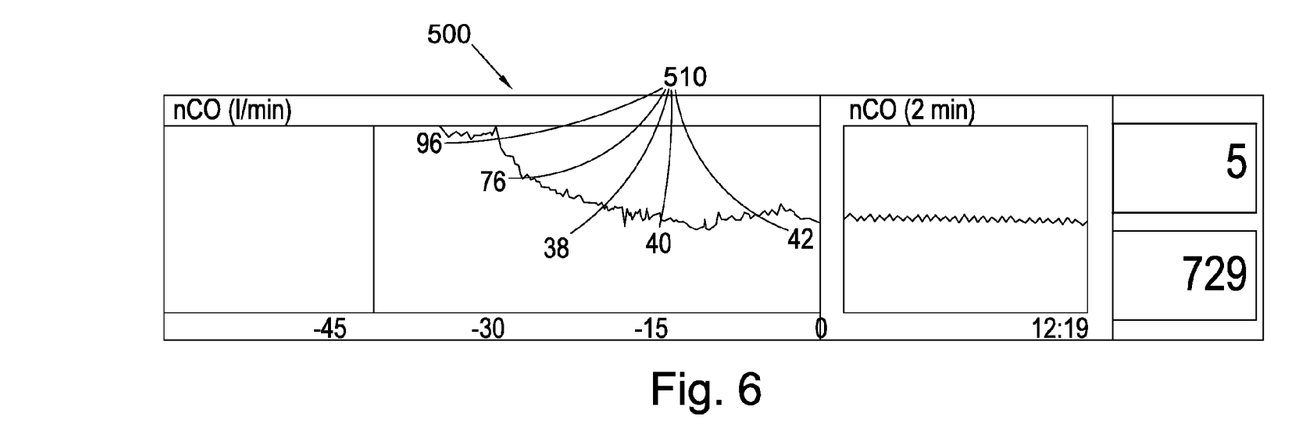
FIG. 6 shows a display panel displaying a plot of a hemodynamic parameter over time and superimposed thereover an indication of the level of consciousness in number format.

The description of embodiments above has focussed on the display of the level of consciousness in the form of a graph. As also discussed above, this is not essential, however, and FIG. 6 shows an alternative or additional way of displaying the level of consciousness. FIG. 6 shows a display panel 500 displaying long and a short term displays of cardiac output. Superimposed over the long term display of the cardiac output are the values of the level of consciousness of the patient at the time point at which the value is displayed. As suggested in FIG. 6, the height at which the value indicating the level of consciousness if displayed above the bottom edge of the display panel can also be indicative of the level of consciousness the patient had at the time, although positioning the numbers in this fashion is optional. It will of course be appreciated that, while FIG. 6 combines the display of cardiac output with the display of numbers representing the level of consciousness of the patient, such a number display can be paired with one or more displays of other hemodynamic parameters, for example with a display of stroke volume, stroke volume variation and mean or systolic blood pressure.

Figure 7:
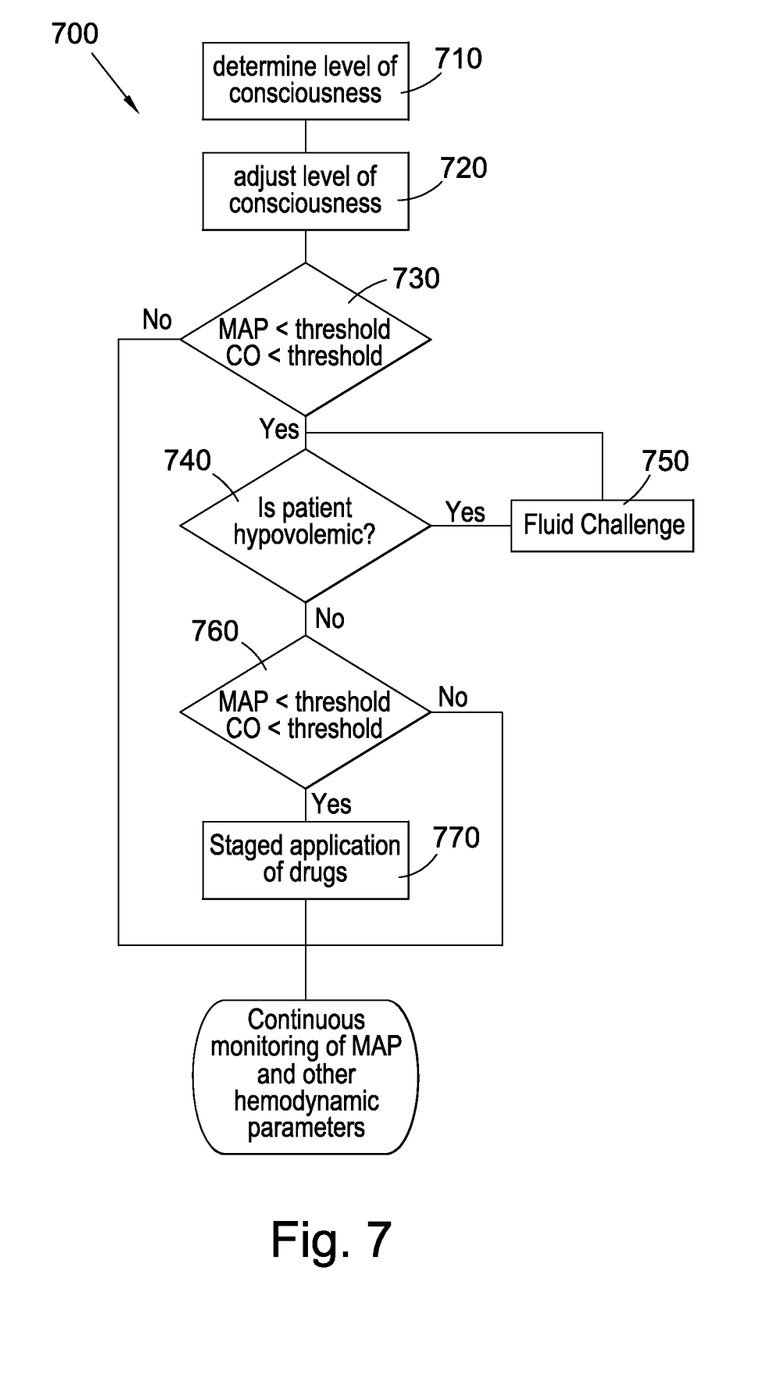
FIG. 7 shows a flow diagram for restoring blood pressure and/or blood flow in a patient following a decrease in blood flow or pressure during anaesthetic induction

FIG. 7 shows a flow chart of a method 700 of increasing a patient's blood pressure and/or blood flow following a change in blood pressure and/or flow during anaesthetic induction. Initially the level of consciousness is determined in a step 710. If the level of consciousness is not within a desired range of values, then the level of consciousness is adjusted in step 720 by altering the amount of anaesthetic or sedative administered.

It is then determined in step 730 if the mean arterial blood pressure, the systolic blood pressure, the cardiac output and/or the stroke volume is below a desired threshold value. In the unlikely event that this is not the case the method is terminated. Should the desired threshold values not be reached by one or more of these parameters, then it is determined if the patient is hypovolemic in step 740. If the patient is hypovolemic, then a fluid challenge of, for example, 200 ml is administered in step 750 and the patients fluid status is again checked in step 740. The administering of fluid challenges can be repeated a number of times if it is repeatedly determined in step 740 that the patient is hypovolemic.

If it is determined in step 740 that the patient is not hypovolemic, then it is again determined in step 760 if the mean arterial blood pressure, the systolic blood pressure, the cardiac output and/or the stroke volume is below the desired threshold value. Should this still be the case, then a staged approach of administering drugs that may be suitable for increasing blood flow and/or blood pressure is used in step 770 to identify which particular drug is suitable to increase blood pressure/blood flow in the particular patient. Drugs having a more time limited effect may be administered first in this staged approach and their effect on blood flow and blood pressure is observed on the monitoring device. Drugs having a more lasting effect may be administered later in this staged approach, if the earlier administered drugs have not shown to have the desired effect, followed again by an observation of their effects.

It will be appreciated that the above description of the present invention is made by way of example only to illustrate the present invention. The person skilled in the art will appreciate that the present invention is not limited by the examples provided above.

The invention claimed is:

1. A monitoring device comprising:
  a part for acquiring a signal indicating a level of consciousness, wherein said signal is a biopotential signal, based on a biopotential signals or a bispectral index signal;
  a part for acquiring an arterial blood pressure signal;
  a display; and
  a processor or processors arranged to record a series of data sets over a period of time, each data set at least comprising a value of said signal indicating a level of consciousness applicable at a time point and a value of said arterial blood pressure signal at the time point;
  wherein the processor or processors are further arranged to determine, based on the series of data sets, a characteristic of one or more of a change in mean arterial blood pressure, in systemic vascular resistance, in cardiac output, in stroke volume, in stroke volume variation and in pulse pressure variation and pleth variability index dependent on the level of consciousness.

2. The device of claim 1, wherein the processor or processors are further arranged to cause the display to display one or more of the said characteristics and an indication of a change in blood pressure and/or another hemodynamic parameter that is to be expected, based on the characteristics, for a unit change in the level of consciousness.

3. The device of claim 1, wherein the processor or processors are arranged to cause the display to display, in one operating mode and for simultaneous viewing, an image showing the blood pressure signal over time, an image showing cardiac output or stroke volume over time, an image showing systemic vascular resistance over time and an image showing the level of consciousness over time based on the signal indicating the level of consciousness.

4. The device of claim 3, wherein the processor or processors are further arranged to, in another operating mode, replace the display of one of the said images with the display of an image showing a response of a hemodynamic parameter to an intervention.

5. The device of claim 3, wherein the processor or processors are arranged to cause the display to display an indication of a current value of a parameter or parameters that is or are displayed in one or more of the images in number format alongside the images.

6. The device of claim 3, wherein the processor or processors are further arranged to display one or more of the images in a time synchronised fashion.

7. The device of claim 1, wherein the device is arranged to store a base line of one or more of the level of consciousness, a value of a blood flow/oxygen delivery signal and the arterial blood pressure signal; and wherein the processor or processors are arranged to display a current and/or past indication of the level of consciousness and/or current and/or past level of one or more of the arterial blood pressure, the cardiac output, the oxygen delivery, the stroke volume and the systemic vascular resistance with reference to a said stored base line or to a base line determined from a said stored base line.

8. The device of claim 1, wherein the data set further comprises one or more of the cardiac output at the time point, the stroke volume at the time point and the systemic vascular resistance at the time point.

9. The device of claim 1, wherein the processor or processors are further arranged to facilitate interpolation between the series of data sets.

10. The device of claim 9, wherein the processor or processors are arranged to fit a curve to said series of data sets.

11. The device of claim 10, wherein the processor or processors are configured to cause the display to display the curve or, if the curve is a linear function, an indication of the gradient of the function.

\* \* \* \* \*